(12) United States Patent
Yoon (10) Patent No.: US 10,260,707 B2
(45) Date of Patent: Apr. 16, 2019

(54) ULTRA VIOLET RAY EMITTING DIODE LIGHTING DEVICE

(71) Applicant: SEOUL VIOSYS CO., LTD., Gyeonggi-do (KR)

(72) Inventor: Joung-Il Yoon, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 122 days.

(21) Appl. No.: 15/533,347

(22) PCT Filed: Nov. 4, 2015

(86) PCT No.: PCT/KR2015/011813
§ 371 (c)(1),
(2) Date: Jun. 5, 2017

(87) PCT Pub. No.: WO2016/089017
PCT Pub. Date: Jun. 9, 2016

(65) Prior Publication Data
US 2018/0010764 A1    Jan. 11, 2018

(30) Foreign Application Priority Data
Dec. 5, 2014 (KR) .......................... 10-2014-0174208

(51) Int. Cl.
*F21V 19/00* (2006.01)
*A61L 2/10* (2006.01)
(Continued)

(52) U.S. Cl.
CPC .............. *F21V 3/06* (2018.02); *A61L 2/088* (2013.01); *A61L 2/10* (2013.01); *A61L 2/26* (2013.01);
(Continued)

(58) Field of Classification Search
CPC .... F21V 3/0409; F21V 19/0015; F21V 29/83; A61L 2/10
See application file for complete search history.

(56) References Cited

U.S. PATENT DOCUMENTS

| 2012/0008316 A1 | 1/2012 | Ivey |
| 2012/0293991 A1 | 11/2012 | Lin |
| 2013/0170196 A1 | 7/2013 | Huang |

FOREIGN PATENT DOCUMENTS

| CN | 202392485 U | 8/2012 |
| JP | 2012141555 A | 5/2002 |

(Continued)

OTHER PUBLICATIONS

Search Report in European Patent Application No. 15864456.7, dated Mar. 27, 2018.

(Continued)

*Primary Examiner* — Joseph L Williams
(74) *Attorney, Agent, or Firm* — Perkins Coie LLP (57) ABSTRACT

Disclosed is an ultraviolet ray emitting diode lighting device. The disclosed invention comprises: an ultraviolet ray emitting diode for emitting ultraviolet rays; a substrate on which an ultraviolet ray emitting diode is mounted; a base on which a space for accommodating the substrate is formed and an electrode pin electrically connected to the substrate is installed; and a cover, which is provided to surround the ultraviolet ray emitting diode and the substrate and is coupled to the base, wherein the base includes a support guide fitted in the substrate to support the substrate on the base so as to restrict movement of the substrate.

20 Claims, 7 Drawing Sheets

(51) Int. Cl.
- *A61L 9/20* (2006.01)
- *F21V 3/06* (2018.01)
- *F21V 29/83* (2015.01)
- *F21K 9/272* (2016.01)
- *F21K 9/278* (2016.01)
- *A61L 2/08* (2006.01)
- *A61L 2/26* (2006.01)
- *F21Y 115/10* (2016.01)
- *F21K 9/90* (2016.01)
- *F21V 15/015* (2006.01)
- *F21V 17/16* (2006.01)
- *F21Y 103/10* (2016.01)

(52) U.S. Cl.
CPC .............. *A61L 9/205* (2013.01); *F21K 9/272* (2016.08); *F21K 9/278* (2016.08); *F21V 19/003* (2013.01); *F21V 19/0015* (2013.01); *F21V 29/83* (2015.01); *A61L 2202/11* (2013.01); *A61L 2209/12* (2013.01); *F21K 9/90* (2013.01); *F21V 15/015* (2013.01); *F21V 17/164* (2013.01); *F21Y 2103/10* (2016.08); *F21Y 2115/10* (2016.08)

(56) References Cited

FOREIGN PATENT DOCUMENTS

| | | |
|---|---|---|
| JP | 2011-070988 A | 4/2011 |
| KR | 101068193 B1 | 9/2011 |
| KR | 10-1091307 B1 | 12/2011 |
| KR | 1020130044718 A | 5/2013 |
| KR | 10-1438729 B1 | 9/2014 |
| KR | 10-2014-0029580 A | 3/2017 |
| WO | 2014001475 A1 | 1/2014 |

OTHER PUBLICATIONS

International Search Report and Written Opinion in International Application No. PCT/KR2015/011813, filed Nov. 4, 2015, Applicant: Seoul Viosys Co., Ltd., dated Mar. 16, 2016, 11 pages.

ULTRA VIOLET RAY EMITTING DIODE LIGHTING DEVICE

CROSS REFERENCE TO RELATED APPLICATIONS

This patent document is a 35 U.S.C. § 371 National Stage application of PCT Application No. PCT/KR2015/011813, filed on Nov. 4, 2015, which further claims the benefits and priorities of prior Korean Patent Application No. 10-2014-0174208, filed on Dec. 5, 2014. The entire disclosures of the above applications are incorporated by reference in their entirety as part of this document.

TECHNICAL FIELD

The present invention relates to a lighting apparatus using a UV LED (light emitting diode) lighting apparatus, and more particularly, a lighting apparatus configured to emit UV light using a UV LED.

BACKGROUND ART

Due to various advantages such as small size, high brightness at low power consumption, long lifespan, and low manufacturing costs, light emitting diodes (LEDs) are used in a display unit or a lighting apparatus which replaces a typical light bulb.

Depending upon luminous characteristics, light emitting diodes can be classified into IR light emitting diodes configured to emit IR light, visible light emitting diodes configured to emit visible light, UV LED (light emitting diode)s configured to emit UV light, and the like.

Among such light emitting diodes, UV LEDs have been applied to a sterilization apparatus with various advantages, such as inexpensiveness, user convenience and high efficiency, in various fields, since effects of UV light in removal of DNA or RNA bacteria were ascertained.

For example, the UV LED is used in a sterilization apparatus provided to various products, such as household refrigerators, warehouse refrigerators, vehicle-mounted refrigerators, kimchi refrigerators, cup sterilizers, shoes deodorizers, and the like, to remove bacteria and odors.

Typically, a lighting apparatus using a light emitting diode is provided in a structure wherein a printed circuit board having a light emitting diode mounted thereon is provided to a socket and a cover formed of a transparent or translucent acryl or glass material surrounds the light emitting diode.

A lighting apparatus using a UV LED requires a cover formed of a material exhibiting high UV light transmittance due to wavelength characteristics of UV light emitted from the UV LED.

Examples of materials for the cover suitable for such a UV LED lighting apparatus include quartz, a poly(methyl methacrylate) (PMMA) resin, and the like, which exhibit high UV light transmittance.

However, despite high UV light transmittance, such materials are not suitable for the UV LED lighting apparatus due to difficulty in machining such as bending and punching, and low machinability.

DISCLOSURE

Technical Problem

Exemplary embodiments of the present invention provide a UV LED lighting apparatus which has improved properties in terms of UV illumination efficiency and assembly performance.

Technical Solution

In accordance with one aspect of the present invention, a UV LED lighting apparatus includes: a UV LED configured to emit UV light; a substrate on which the UV LED is mounted; a base having an accommodation space formed therein to receive the substrate and provided with electrode pins electrically connected to the substrate; and a cover disposed to surround the UV LED and the substrate and coupled to the base, wherein the base includes a support guide press-fitted with the substrate and supporting the substrate with respect to the base so as to restrict movement of the substrate.

Preferably, the support guide includes a rib protruding into the base having the accommodation space formed therein; and a coupling recess formed in the rib and receiving the substrate therein.

Preferably, the substrate is formed with a latch groove at a portion of the substrate inserted into the coupling recess; and the support guide further includes a hook protruding from the rib towards the coupling recess and fitted into the latch groove to secure the substrate to the support guide.

Preferably, the UV LED lighting apparatus further includes a resilient member provided to the coupling recess and providing compressive force to force the substrate to be brought into close contact with the hook fitted into the substrate.

Preferably, the UV LED lighting apparatus further includes a fastening member coupled to the base to penetrate the base and securing the substrate to the base.

Preferably, the base is formed therethrough with a guide hole through which the fastening member passes when penetrating the base; the substrate is formed therethrough with a fastening hole through which the fastening member passes when penetrating the base through the guide hole; and the fastening member is coupled to the base through coupling to the guide hole and is coupled to the substrate through coupling to the fastening hole to secure the substrate to the base.

Preferably, the fastening member restricts movement of the substrate in a different direction than a direction of the support guide restricting movement of the substrate and couples the substrate to the base.

Preferably, the cover is press-fitted into the base, and the base is provided with a protrusion protruding into a gap between the base and the cover and compressing the cover press-fitted into the base.

Preferably, the cover is press-fitted into the base, and the base is provided with an O-ring member fitted into a gap between the base and the cover and forcing the cover to be interference-fitted into the base.

Preferably, the cover includes at least one of quartz and a poly(methyl methacrylate) resin exhibiting high UV transmittance.

Preferably, the electrode pins are provided to the base through insert injection molding.

Preferably, each of the electrode pins includes an insertion hole formed therein and receiving a connection wire electrically connecting the substrate to the electrode pin.

Preferably, the UV LED emits UV light having a peak wavelength of 340 nm to 400 nm.

Preferably, the UV LED emits UV light having a wavelength of 365 nm.

Preferably, the UV LED lighting apparatus further includes: a first connection wire electrically connecting one of the pair of electrode pins to a surface of the substrate in the accommodation space; and a second connection wire electrically connecting the other electrode pin to a back surface of the substrate in the accommodation space.

Advantageous Effects

According to exemplary embodiments of the present invention, a UV LED lighting apparatus is provided in the form of a finished product through assembly of a substrate, bases, and a cover so as to make it unnecessary to perform operation of punching, accessory attachment or deformation with respect to the cover, and thus can provide improved illumination effects using the cover having high UV transmittance.

In addition, the UV LED lighting apparatus according to the exemplary embodiments can be easily assembly without separate post machining with respect to the cover and separate bonding with respect to each component, thereby reducing work time and costs for manufacture of products through improvement in assembly performance.

BEST MODE

Hereinafter, exemplary embodiments of the present invention will be described in detail with reference to the accompanying drawings. It should be understood that the drawings are not to precise scale and may be exaggerated in thickness of lines or size of components for descriptive convenience and clarity only. In addition, the terms used herein are defined by taking functions of the present invention into account and can be changed according to user or operator custom or intention. Therefore, definition of the terms should be made according to the overall disclosure set forth herein.

Figure 1:
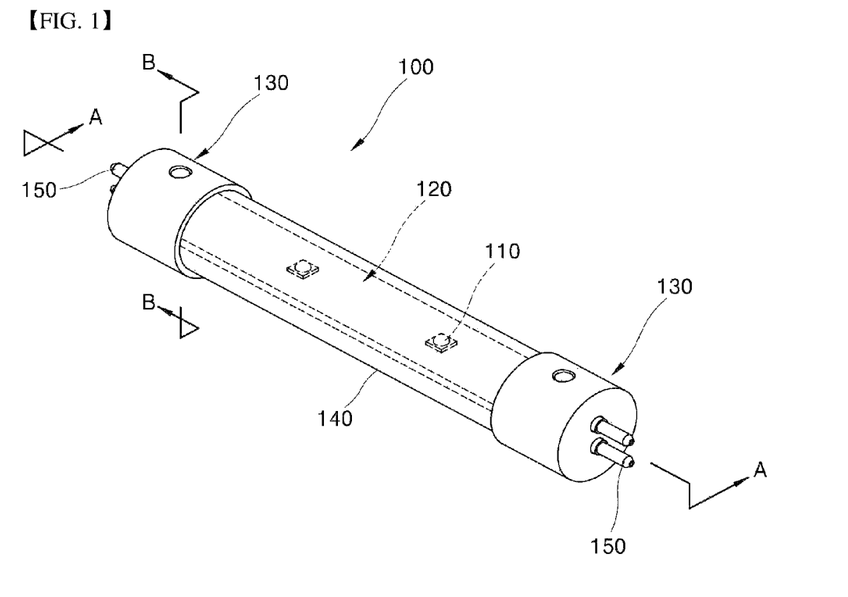
FIG. 1 is a perspective view of a UV LED lighting apparatus according to one exemplary embodiment of the present invention.
Figure 2:
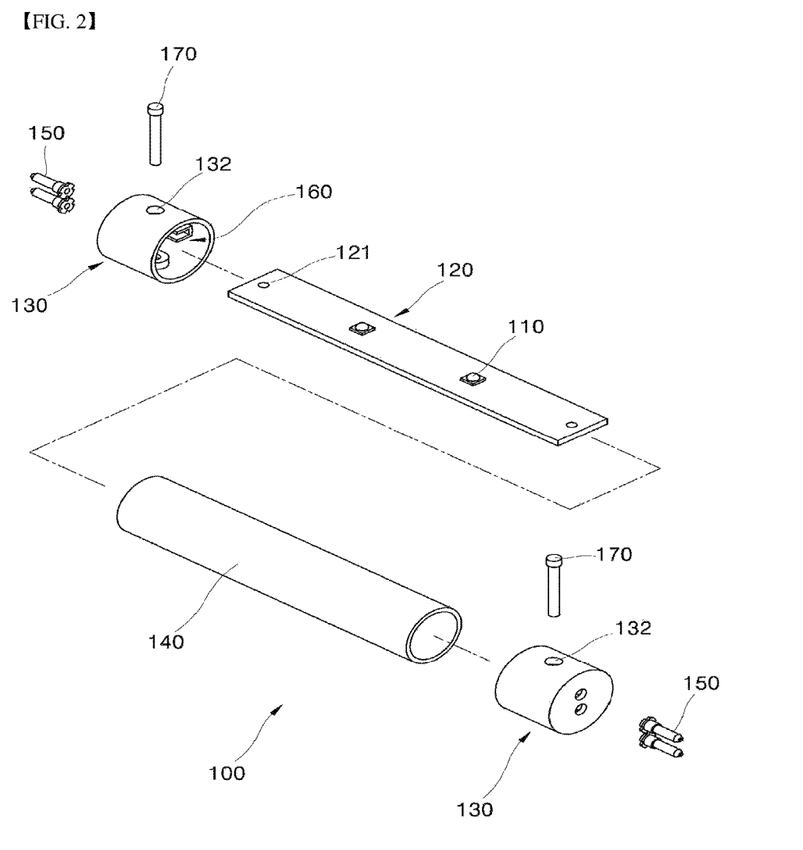
FIG. 2 is an exploded perspective view of the UV LED lighting apparatus shown in FIG. 1.

FIG. 1 is a perspective view of a UV LED lighting apparatus according to one exemplary embodiment of the present invention and FIG. 2 is an exploded perspective view of the UV LED lighting apparatus shown in FIG. 1.

Referring to FIG. 1 and FIG. 2, a UV LED lighting apparatus 100 according to one exemplary embodiment of the present invention includes a UV LED (light emitting diode) 110, a substrate 120, bases 130, and a cover 140.

The UV LED 110 is configured to emit UV light. The UV LED 110 may be configured to emit UV light having a peak wavelength in the range of 340 nm to 400 nm, more specifically in the range of 360 nm to 370 nm.

Particularly, not only is UV light having a wavelength of 365 nm a powerful insect attractant, but also has high effects in decomposition of toxic substances, contaminants, or odors through promotion of catalytic reaction of a photocatalyst.

In this embodiment, the UV LED 110 is configured to emit UV light having a wavelength of 365 nm and the UV LED lighting apparatus 100 including the UV LED 110 may be used for attraction of insects and decomposition of toxic substances, contaminants or odors.

The substrate 120 is a structure for mounting the UV LED 110 thereon. Such a substrate 120 has a length determined in consideration of a region to be irradiated with UV light through the UV LED lighting apparatus 100.

The substrate 120 is provided in the form of a plate having a predetermined thickness and strength so as to prevent warpage due to the weight thereof and the weight of the UV LED 110, with only opposite ends of the substrate 120 supported.

According to this embodiment, a plurality of UV LEDs 110 is mounted on the substrate 120 to be arranged at certain intervals thereon.

On the substrate 120, the UV LED 110 may be mounted in the form of a metal can or an injection type lead frame package which can be mounted on the surface of the substrate 120, may be mounted in a through-hole mounting type, or may be mounted in a bare chip or flip-chip type.

In addition, the UV LED 110 may be provided to a sub-mount, which is used to improve heat dissipation or electrical characteristics.

The bases 130 are provided to the opposite ends of the substrate 120 in the longitudinal direction, respectively. Each of the bases 130 has an accommodation space formed therein and receiving the substrate 120, specifically, one end of the substrate 120, therein.

Each of the bases 130 is provided with electrode pins 150 electrically connected to the substrate 120.

The electrode pins 150 are electrically connected to a socket (not shown), on which the UV LED lighting apparatus 100 will be mounted, to receive electric power supplied from a power source. Such electrode pins 150 serve as media which supply electric power supplied from a power source to the substrate 120 and the UV LED 110 mounted thereon through connection wires 101,105 (see FIG. 3). Details of the electrode pins 150 will be described below.

The cover 140 is disposed to surround the UV LED 110 and the substrate 120. The cover 140 is coupled to the bases 130 by press-fitting both ends of the cover 140 into the bases 130, respectively.

According to this embodiment, the cover 140 may be formed of a material exhibiting high UV light transmittance, for example, at least one of a poly(methyl methacrylate) (PMMA) resin having a high monomer content and quartz. In addition, the cover 140 may be formed of a flexible material having high UV light transmittance.

Since the cover 140 formed of such a material exhibits high UV light transmittance to allow UV light emitted from the UV LED 110 to pass therethrough in a high ratio, the cover 140 can protect the UV LED 110 and the substrate 120 from impact and contaminants while improving illumination effects using UV light.

Figure 3:
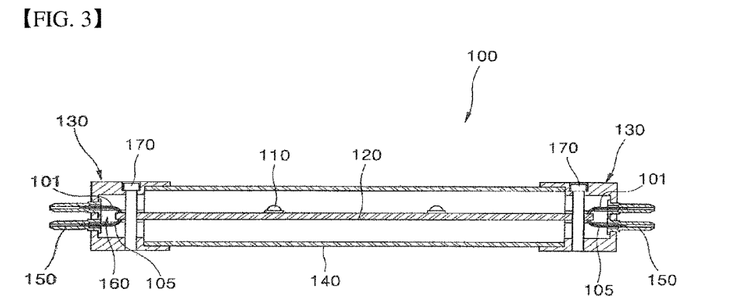
FIG. 3 is a cross-sectional view taken along line "A-A" of FIG. 1.
Figure 4:
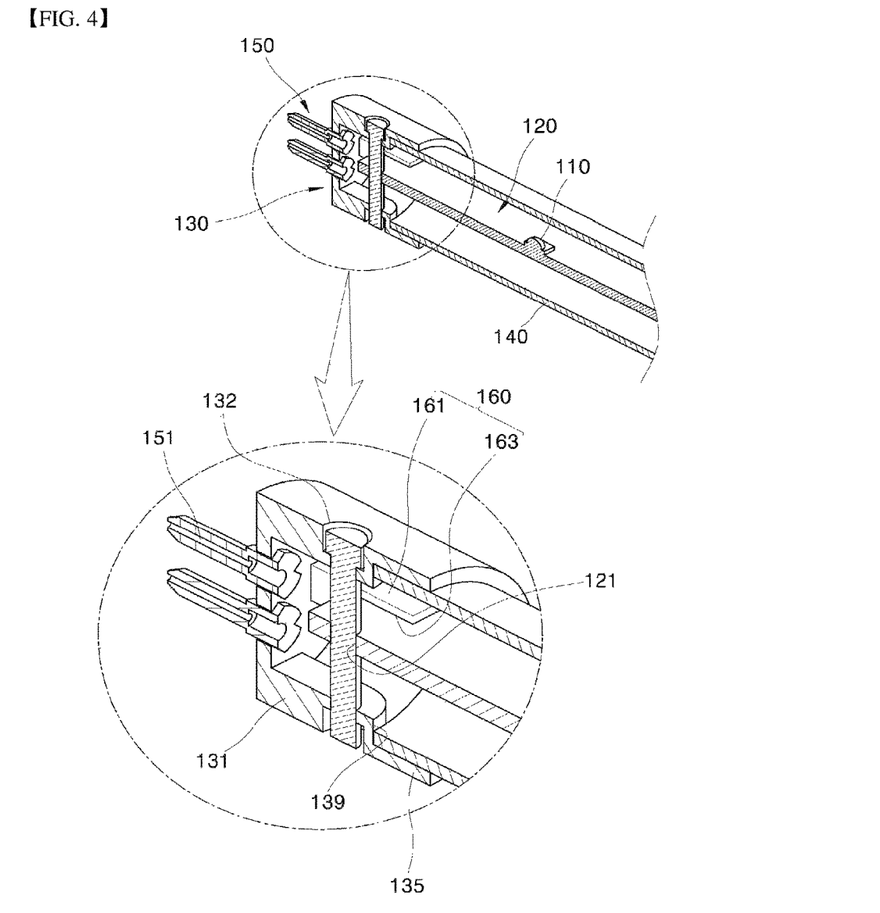
FIG. 4 is a partially enlarged sectional view of the UV LED lighting apparatus shown in FIG. 3.

FIG. 3 is a cross-sectional view taken along line "A-A" of FIG. 1 and FIG. 4 is a partially enlarged sectional view of the UV LED lighting apparatus shown in FIG. 3.

Referring to FIG. 3 and FIG. 4, each of the bases 130 is divided into an electrode pin coupling portion 131 to which the electrode pins 150 are coupled, and a cover coupling portion 135 to which the cover 140 is coupled.

The cover coupling portion 135 has a greater inner diameter than the electrode pin coupling portion 131 and steps 139 are formed between the electrode pin coupling portion 131 and the cover coupling portion 135.

The cover 140 is press-fitted into the bases 130 after being inserted into the cover coupling portion 135, and a coupling location between each of the bases 130 and the cover 140 can be guided by interference between the ends of the cover 140 and the steps 139.

That is, coupling between the cover 140 and the bases 130 can be completed simply by inserting the cover 140 into the bases 130 disposed at opposite sides of the cover 140.

Each of the bases 130 is provided with support guides 160. The support guides 160 are fitted into the substrate 120 and support the substrate 120 with respect to the base 130 so as to restrict movement of the substrate 120.

According to this embodiment, each of the support guides 160 includes a rib 161 and a coupling recess 163.

The rib 161 protrudes into the base 130 having the accommodation space formed therein, specifically, into the electrode pin coupling portion 131. The rib 161 protrudes parallel to the transverse direction of the substrate 120 and a pair of ribs 161 is disposed to face each other in each of the bases 130 in the protruding direction thereof.

In this embodiment, the pair of ribs 161 is illustrated as being arranged orthogonal to an arrangement direction of the electrode pins 150.

The coupling recess 163 is formed in each of the ribs 161. One end of the substrate 120 is slidably inserted into the coupling recess 163 and interference coupling between the substrate 120 and each of the support guides 160 can be achieved through insertion of the substrate 120 into the coupling recess.

By such interference coupling between the substrate 120 and the support guides 160, the substrate 120 can be supported by the bases 130 such that movement of the substrate 120 can be restricted in the thickness direction (hereinafter, "vertical direction") thereof.

According to this embodiment, the UV LED lighting apparatus 100 may further include a fastening member 170, which passes through the base 130 to be coupled to the base 130 so as to secure the substrate 120 to the base 130.

A guide hole 132 is formed through the base 130 to allow the fastening member 170 to pass therethrough when penetrating the base 130, and a fastening hole 121 is formed through the substrate 120 to allow the fastening member 170 to pass therethrough when penetrating the base 130 through the guide hole 132.

The guide hole 132 and the fastening hole 121 are formed through the base 130 and the substrate in a penetrating direction of the fastening member 170 passing through the base 130, for example, in the thickness direction of the substrate 120, respectively.

The fastening member 170 is coupled to the base 130 through coupling to the guide hole 132 and is coupled to the substrate 120 through coupling to the fastening hole 121, thereby securing the substrate 120 to the base 130.

In this way, the fastening member 170 secures the substrate 120 to the base 130 such that movement of the support guide 160 is restricted in a direction other than the direction of restricting movement of the substrate 120.

For example, when the fastening member 170 secures the substrate 120 to the base 130 so as to restrict vertical movement of the support guide 160, the fastening member 170 may secure the substrate 120 to the base 130 so as to restrict movement of the substrate 120 in the longitudinal direction (hereinafter, "horizontal direction") thereof.

In addition, the fastening member 170 may secure the substrate 120 to the base 130 so as to restrict movement of the substrate 120 in the width direction (hereinafter "transverse direction") thereof by adjusting a gap between the support guides 160 into which the substrate 120 is inserted.

The electrode pins 150 are provided to the electrode pin coupling portion 131 of the base 130 and pass through one side of the base 130 in the longitudinal direction such that one side of each of the electrode pin 150 is exposed to the accommodation space of the base 130 and the other side thereof is exposed outside the base 130.

By way of example, the electrode pins 150 may be integrally formed with the base 130 through insert injection to the base 130, which is formed by injection molding.

The structure wherein the electrode pins 150 are integrally formed with the base 130 allows not only reduction in the number of components but also removal of a process of assembling the electrode pins 150 to the base 130, thereby reducing labor and costs for manufacture of the UV LED lighting apparatus 100.

Each of the electrode pins 150 provided to the base 130 is electrically connected at one side thereof to the substrate 120 via a connection wire 101 or 105. In addition, the other side of the electrode pin 150 exposed to the outside of the base 130 is electrically connected to a socket (not shown).

According to this embodiment, each of the electrode pins 150 is formed with an insertion hole 151 into which the connection wire 101 or 105 is inserted. Connection between the electrode pins 150 and the connection wires 101,105 may be achieved as follows.

Specifically, with the connection wire 101 or 105 inserted into the insertion holes 151 to pass through the electrode pins 150, a portion of the connection wire 101 or 105 protruding from the other side of the electrode pins 150 is trimmed and then the connection wire 101 or 105 is soldered to tips of the electrode pins 150 while inwardly compressing each of the electrode pins 150 such that the electrode pins 150 are brought into contact with the connection wire 101 or 105, thereby achieving connection between the electrode pins 150 and the connection wires 101, 105.

According to this embodiment, each of the bases 130 is provided with the pair of electrode pins 150. In each of the bases 130, the electrode pins 150 are separated a predetermined distance from each other in a perpendicular direction with respect to the longitudinal direction of the substrate 120.

One of the electrode pins 150 is disposed adjacent the surface of the substrate 120 on which the UV LED 110 is placed, and the other electrode pin 150 is disposed adjacent the back surface of the substrate 120.

The connection wires 101, 105 connect the electrode pins 150 to the substrate 120, and include a first connection wire 101 and a second connection wire 105.

The first connection wire 101 electrically connects one of the electrode pins 150, that is, the electrode pin 150 disposed adjacent the surface of the substrate 120, to the surface of the substrate 120.

The second connection wire 105 electrically connects the other electrode pin 150, that is, the electrode pin disposed adjacent the back surface of the substrate 120, to the back surface of the substrate 120.

Connection between one of the electrode pins 150 and the substrate 120 is achieved through the surface of the substrate 120 and connection between the other electrode pin 150 and the substrate 120 is achieved through the back surface of the substrate 120.

Such a connection structure between the electrode pins 150 and the substrate 120 allows connection between the pair of electrode pins 150 and the substrate 120 to be achieved in different accommodation spaces divided by the substrate 120.

That is, the structure wherein the electrode pins 150 are separated from each other in the perpendicular direction with respect to the surface of the substrate 120 allows connection between the pair of electrode pins 150 and the substrate 120 to be achieved in the different accommodation spaces divided by the substrate 120, thereby securing a sufficient space for connection of the connection wires 101, 105 to the substrate 120.

Figure 5:
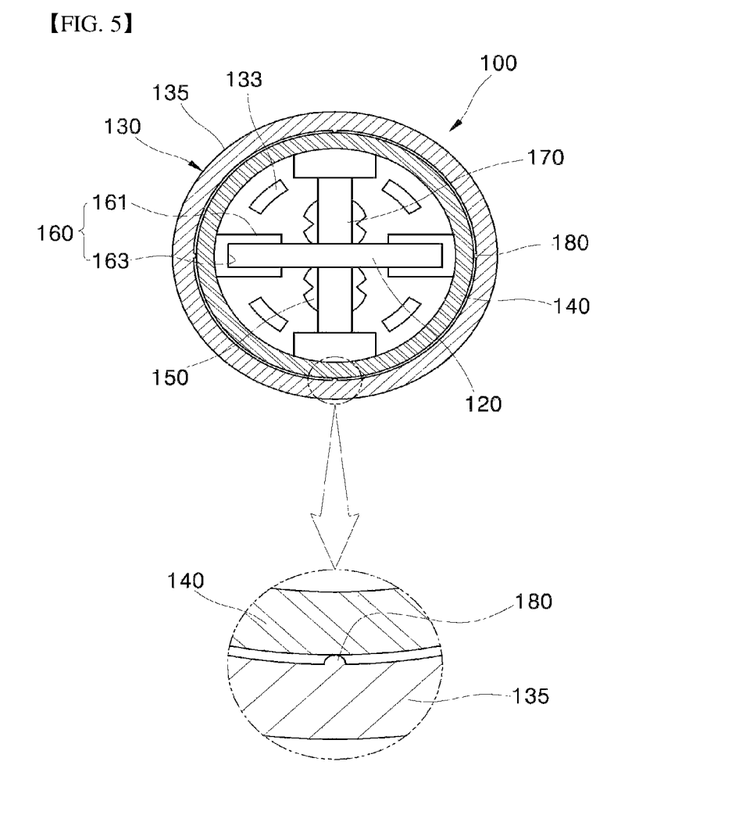
FIG. 5 is a cross-sectional view taken along line "B-B" of FIG. 1.
Figure 6:
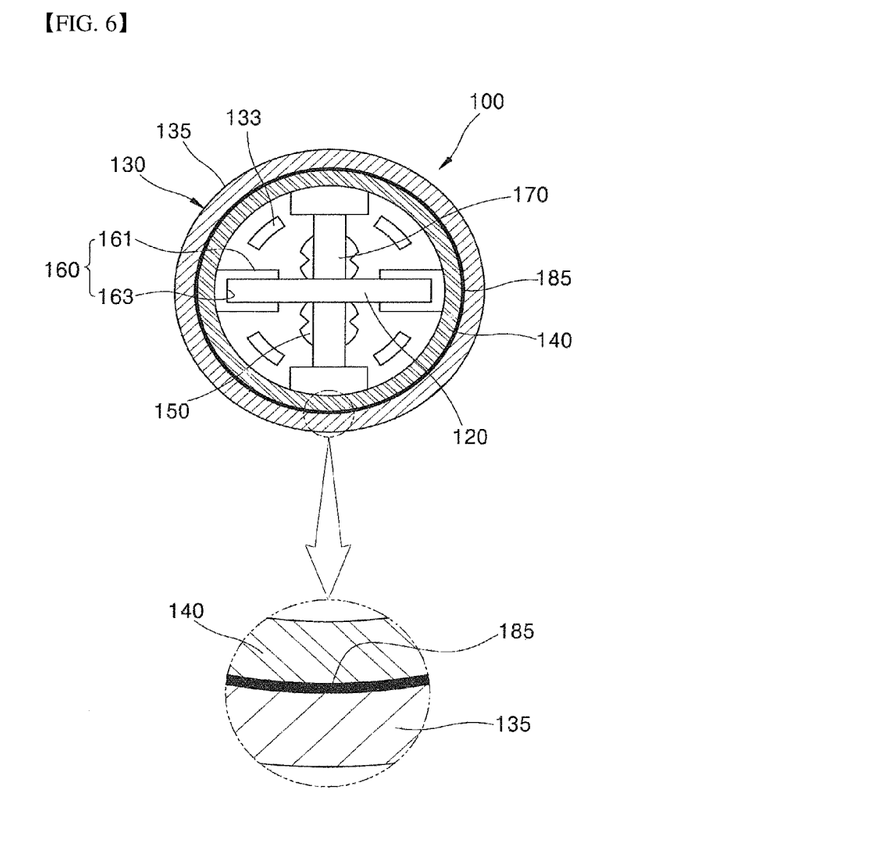
FIG. 6 is a cross-sectional view of another example of coupling between a cover and a base shown in FIG. 5.

FIG. 5 is a cross-sectional view taken along line "B-B" of FIG. 1 and FIG. 6 is a cross-sectional view of another example of coupling between the cover and the base shown in FIG. 5.

Referring to FIG. 5, the base 130 may have pores 133. The pores 133 may be formed to penetrate the electrode pin coupling portion 131 and may be arranged at certain intervals in the electrode pin coupling portion 131.

The pores 133 allow heat generated during UV light emission of the UV LED 110 to be discharged therethrough, thereby preventing excessive increase in temperature of the UV LED lighting apparatus 100.

The UV LED lighting apparatus 100 according to this embodiment may further include protrusions 180.

The protrusions 180 are formed on an inner surface of each of the bases 130, specifically on an inner peripheral surface of the cover coupling portion 135.

According to this embodiment, the protrusions 180 are formed between the base 130 and the cover 140 to overlap the cover 140 press-fitted into the base 130.

With this structure, the protrusions 180 compress the cover 140 press-fitted into the base 130 to allow interference fit between the base 130 and the cover 140, thereby improving coupling between the base 130 and the cover 140.

In another example, the UV LED lighting apparatus 100 may include an O-ring member 185, as shown in FIG. 6.

The O-ring member 185 is formed in a ring shape of a resilient material and is disposed between the base 130 and the cover 140 coupled to each other.

The O-ring member 185 has a greater thickness than a gap between the base 130 and the cover 140 and is interposed between the base 130 and the cover 140 to allow interference fit between the base 130 and the cover 140, thereby improving coupling force between the base 130 and the cover 140.

Such an O-ring member 185 allows easy replacement when damaged and can effectively shield a coupled portion between the base 130 and the cover 140, thereby improving waterproof and dust-proof performance of the UV LED lighting apparatus 100.

Next, operation and effects of the UV LED lighting apparatus according to this embodiment will be described with reference to FIG. 1 to FIG. 6.

As shown in FIG. 1 to FIG. 4, the UV LED lighting apparatus 100 according to this embodiment can be generally divided into the substrate 120 on which the UV LED 110 is mounted, the bases 130, and the cover 140.

Each of the components constituting the UV LED lighting apparatus 100 may be assembled as follows.

The substrate 120 may be provided to the bases 130 to be supported by the bases 130 by press-fitting the substrate 120 into the support guides 160.

Then, the fastening member 170 is coupled to each of the bases 130 so as to penetrate the base 130, whereby the substrate 120 can be more firmly fastened to the bases 130.

Here, movement of the substrate 120 in the vertical direction and the transverse direction is restricted by the support guides 160 coupled to both sides of the substrate 120 and movement of the substrate 120 in the horizontal direction is restricted by the fastening member 170 coupled to the substrate 120 through the substrate 120.

As a result, the substrate 120 can be stably coupled to the base 130 while movement of the substrate 120 is restricted in various directions.

Coupling between each of the bases 130 and the cover 140 can be easily achieved simply by inserting the cover 140 into the cover coupling portion 135.

Here, the protrusions 180 formed on the inner peripheral surface of the cover coupling portion 135 are disposed between the base 130 and the cover 140 to compress the cover 140, or the O-ring member 185 is fitted into the gap between the base 130 and the cover 140, as shown in FIG. 5 and FIG. 6.

Accordingly, since interference fit between the bases 130 and the cover 140 can be achieved to improve fastening force between the bases 130 and the cover 140, coupling between the bases 130 and the cover 140 can be effectively achieved simply by inserting the cover 140 into the cover coupling portion 135.

That is, the substrate 120 and the cover 140 can be stably coupled to the bases 130 and assembly of the UV LED lighting apparatus 100 can be completed without additional machining processes, such as a process of punching holes for coupling the fastening member to the cover 140, a process of attaching accessories to the cover 140 to couple the cover 140 to other members, a process of deforming the cover 140 in order to couple the cover 140 to other members, and the like.

According to this embodiment, the cover 140 is formed of a poly(methyl methacrylate) resin or quartz, which exhibit high UV light transmittance.

As a material for the cover 140, although the poly(methyl methacrylate) resin or quartz allows UV light emitted from the UV LED 110 to pass therethrough in a high ratio due to high UV transmittance thereof, the poly(methyl methacrylate) resin or quartz has difficulty in machining, such as bending and punching, and low machinability due to characteristics thereof.

In order to solve such problems, the UV LED lighting apparatus 100 according to this embodiment is provided in the form a finished product through assembly of the substrate 120, the base 130, and the cover 140 so as to make it unnecessary to perform operation of punching, accessory attachment or deformation with respect to the cover 140, and thus can provide improved illumination effects using the cover 140 having high UV transmittance.

Furthermore, the UV LED lighting apparatus 100 according to this embodiment can be easily assembled without separate post machining with respect to the cover 140 and separate bonding with respect to each component, thereby reducing work time and costs for manufacture of products through improvement in assembly performance.

Figure 7:
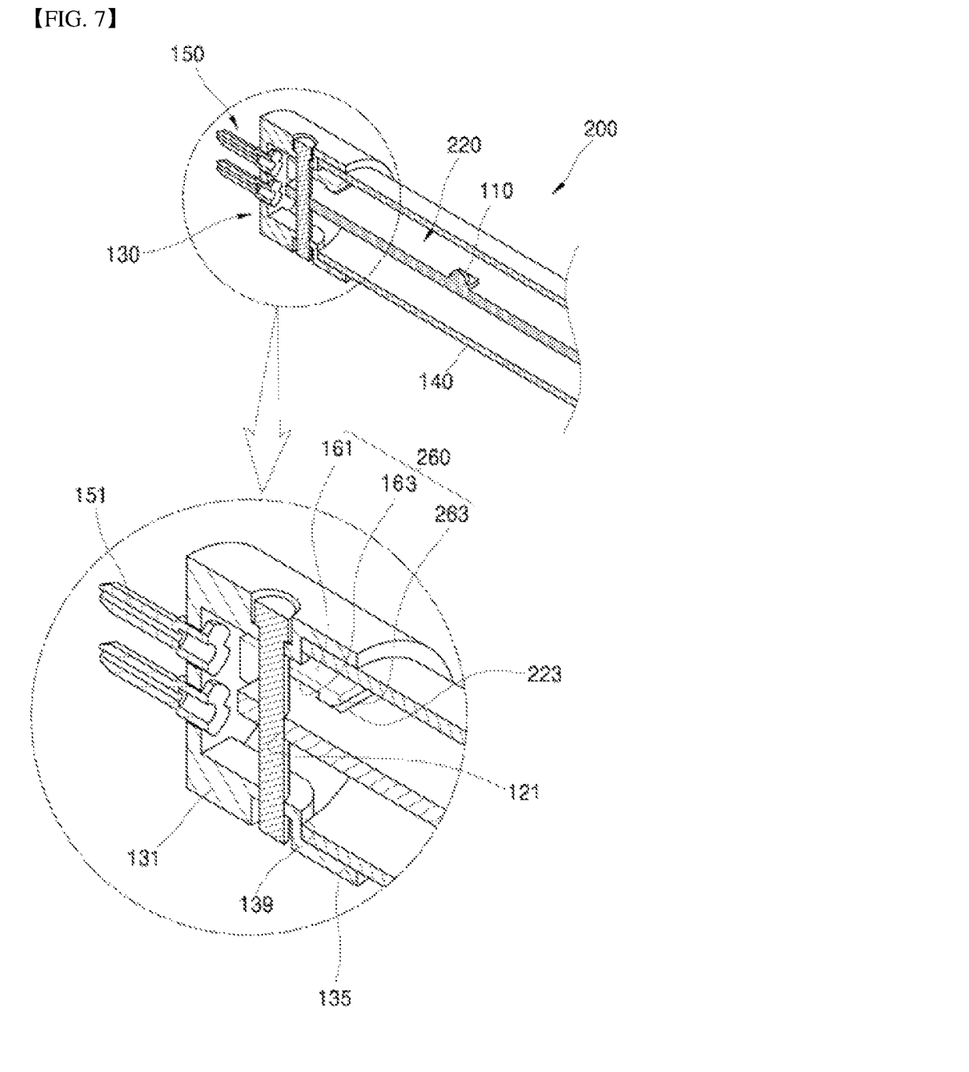
FIG. 7 is a cross-sectional view of a UV LED lighting apparatus according to another exemplary embodiment of the present invention.
Figure 8:
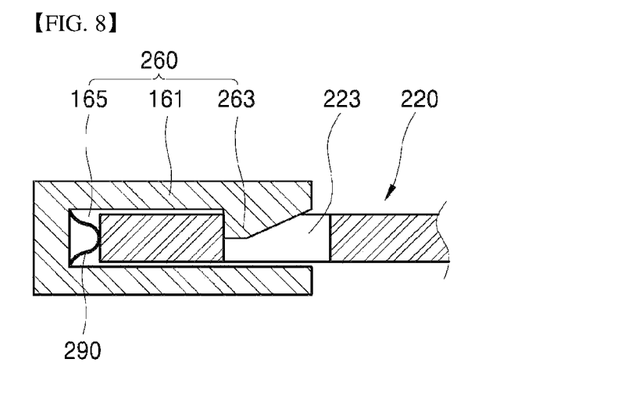
FIG. 8 is a partially enlarged sectional view of the UV LED lighting apparatus shown in FIG. 7.

FIG. 7 is a cross-sectional view of a UV LED lighting apparatus according to another exemplary embodiment of the present invention and FIG. 8 is a partially enlarged sectional view of the UV LED lighting apparatus shown in FIG. 7.

Hereinafter, operation and effects of the UV LED lighting apparatus according to the other exemplary embodiment will be described with reference to FIG. 7 and FIG. 8.

The same or similar components of the UV LED lighting apparatus according to this embodiment to those of the UV LED lighting apparatus according to the above exemplary embodiment are denoted by the same reference numerals and detailed descriptions thereof are omitted.

Referring to FIG. 7 and FIG. 8, a UV LED lighting apparatus 200 according to this embodiment further includes features for improving fastening force between support guides 260 and a substrate 220.

According to this embodiment, the substrate 220 is provided with latch grooves 223 at portions of the substrate 220 inserted into the coupling recesses 163, and each of the support guides 260 is provided with a hook 263.

The latch grooves 223 are provided to opposite ends of the substrate 220 corresponding to the portions of the substrate inserted into the coupling recesses 163, respectively. Such latch grooves 223 may be formed through the substrate 220 or may be concavely formed thereon.

The hook 263 is formed on the support guide 260. More specifically, the hook 263 is formed on one end of the rib 161 to protrude from the rib 161 towards the coupling recess 163. In this embodiment, the rib 161 having the hook 263 can be resiliently deformed in the vertical direction.

The hook 263 is fitted into the latch groove 223 to secure the substrate 220 to the support guide 260 when the substrate 220 is completely inserted into the coupling recess 163.

That is, as the hook 263 is fitted into the latch groove 223, interference between the hook 263 and the substrate 220 occurs when external force is applied to the substrate 220 in a direction of releasing the substrate 220 from the support guide 260, such that the substrate 220 can be firmly secured to the support guide 260 by restricting movement of the substrate 220 in the horizontal direction.

With such coupling between the hook 263 and the latch groove 223, the substrate 220 can be primarily coupled to the base 130 simply by inserting the substrate 220 into the support guide 260 without fastening the fastening member 170, thereby improving assembly convenience while reducing time for product assembly.

The UV LED lighting apparatus 200 according to this embodiment may further include a resilient member 290.

The resilient member 290 may be a spring, such as a coil spring, a leaf spring, and the like, and is disposed on an inner wall of the support guide 260, on which the coupling recess 163 is formed, to provide compressive force in the horizontal direction.

Such a resilient member 290 provides compressive force to force the substrate 220 to be brought into close contact with the hook 263 when the hook 263 is fitted into the substrate 220.

With such operation of the resilient member 290, the substrate 220 can be more firmly coupled to the support guide 260 instead of dangling inside the support guide 260.

Although not shown in the drawings, the substrate 220 can be secured by restricting movement of the substrate 220 in the horizontal direction through operation of the hook 263 and the resilient member 290 without the fastening member 170, or by restricting movement of the substrate in the vertical direction through adjustment of the shape and location of the support guide 260 so as to make vertical and transverse gaps of the rib 161 identical to the thickness and width of the substrate 120.

Although some exemplary embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the present invention.

LIST OF REFERENCE NUMERALS 100, 200: UV LED lighting apparatus
101: first connection wire
105: second connection wire
110: UV LED
120, 220: substrate
121: fastening hole
130: base
131: electrode pin coupling portion
132: guide hole
133: pore
135: cover coupling portion
139: step
140: cover
150: electrode pin
151: insertion hole
160, 260: support guide
161: rib
163: coupling recess
170: fastening member
180: protrusion
185: O-ring member
223: latch groove
263: hook
290: resilient member

The invention claimed is:

1. An ultraviolet (UV) light emitting diode (LED) lighting apparatus comprising:
an UV LED configured to emit UV light;
a substrate on which the UV LED is mounted;
a base having an accommodation space formed therein to receive the substrate and provided with a pair of electrode pins electrically connected to the substrate; and
a cover disposed to surround the UV LED and the substrate and coupled to the base,
wherein the base comprises a support guide structured to support the substrate so as to restrict movement of the substrate, the substrate fitted into the support guide.

2. The UV LED lighting apparatus according to claim 1, wherein the support guide comprises:
a rib protruding into the accommodation space of the base; and
a coupling recess formed in the rib and receiving the substrate therein.

3. The UV LED lighting apparatus according to claim 2, wherein the substrate is formed with a latch groove at a portion of the substrate inserted into the coupling recess; and the support guide further comprises a hook protruding from the rib towards the coupling recess and fitted into the latch groove to secure the substrate to the support guide.

4. The UV LED lighting apparatus according to claim 3, further comprising:
a resilient member provided at the coupling recess and providing compressive force to allow the substrate to be brought into close contact with the hook.

5. The UV LED lighting apparatus according to claim 1, further comprising:
a fastening member coupled to the base to penetrate the base and securing the substrate to the base.

6. The UV LED lighting apparatus according to claim 5, wherein the base is formed with a guide hole through which the fastening member passes when penetrating the base;
the substrate is formed with a fastening hole through which the fastening member passes when penetrating the base through the guide hole; and
the fastening member is coupled to the base through coupling to the guide hole and is coupled to the substrate through coupling to the fastening hole to secure the substrate to the base.

7. The UV LED lighting apparatus according to claim 5, wherein the fastening member restricts movement of the substrate in a different direction than a direction that the support guide restrict the movement of the substrate and couples the substrate to the base.

8. The UV LED lighting apparatus according to claim 1, wherein the cover is fitted into the base, and the base is provided with a protrusion protruding into a gap between the base and the cover and compressing the cover fitted into the base.

9. The UV LED lighting apparatus according to claim 1, wherein the cover is fitted into the base, and the base is provided with an O-ring member fitted into a gap between the base and the cover and forcing the cover to be fitted into the base.

10. The UV LED lighting apparatus according to claim 1, wherein the cover comprises at least one of quartz and a poly(methyl methacrylate) resin exhibiting high UV transmittance.

11. The UV LED lighting apparatus according to claim 1, wherein the electrode pin is provided to the base through insert injection molding.

12. The UV LED lighting apparatus according to claim 1, wherein the electrode pin comprises an insertion hole formed therein and receiving a connection wire electrically connecting the substrate to the electrode pin.

13. The UV LED lighting apparatus according to claim 1, wherein the UV LED emits UV light having a peak wavelength of 340 nm to 400 nm.

14. The UV LED lighting apparatus according to claim 13, wherein the UV LED emits UV light having a wavelength of 365 nm.

15. The UV LED lighting apparatus according to claim 1, further comprising:
a first connection wire electrically connecting one of the pair of electrode pins to a surface of the substrate in the accommodation space; and
a second connection wire electrically connecting the other electrode pin to a back surface of the substrate in the accommodation space.

16. An ultraviolet (UV) light emitting diode (LED) lighting apparatus comprising:
bases provided at two opposing sides of the UV LED lighting apparatus;
a substrate supported by the bases, wherein the bases restrict a movement of the substrate in a first direction; and
UV LEDs arranged on the substrate and spaced apart from one another, each UV LED configured to emit light UV light;
wherein each base includes an electrode pin integrally formed with the base and protruding from the base toward an outside of the base, the electrode pin structured to be coupled with the substrate and to provide an electric power to the UV LEDs.

17. The UV LED lighting apparatus according to claim 16, wherein the each base includes an additional electrode pin separated from the electrode pin by a predetermined distance in a perpendicular direction with respect to a longitudinal direction of the substrate.

18. The UV LED lighting apparatus according to claim 17, wherein the electrode pin and the additional electrode pin of the bases are coupled to different surfaces of the substrate.

19. The UV LED lighting apparatus according to claim 16, wherein the each base has ribs protruding from top and bottom to support the substrate, the substrate being fitted into a space between the ribs.

20. The UV LED lighting apparatus according to claim 16, wherein the each base further includes a fastening member formed to connect a top and a bottom of the base, the fastening member structured to support the substrate to the base by restricting movement of the substrate in a second direction different from the first direction.

* * * * *